United States Patent [19]
Kang et al.

[11] 4,129,579
[45] Dec. 12, 1978

[54] PREPARATION OF 2,3-DIHYDROFURAN

[75] Inventors: Jung W. Kang, Clinton; William L. Hergenrother, Akron, both of Ohio

[73] Assignee: The Firestone Tire & Rubber Company, Akron, Ohio

[21] Appl. No.: 829,364

[22] Filed: Aug. 31, 1977

Related U.S. Application Data

[60] Continuation-in-part of Ser. No. 725,603, Sep. 22, 1976, abandoned, which is a division of Ser. No. 629,168, Nov. 5, 1975, abandoned.

[51] Int. Cl.$^2$ ............................................. C07D 307/28
[52] U.S. Cl. ............................ 260/346.11; 260/347.8
[58] Field of Search ..................................... 260/346.11

[56] References Cited
PUBLICATIONS

Botteghi et al., Journal of Organic Chemistry, vol. 37, No. 11 (1972), pp. 1835–1838.
Botteghi, Gazzetta Chimica Italiana, vol. 105, (1975), p. 233–245.

*Primary Examiner*—Henry R. Jiles
*Assistant Examiner*—Bernard Dentz

[57] ABSTRACT

2,3-Dihydrofuran is prepared from 2-hydroxytetrahydrofuran by dehydration utilizing specific catalysts selected from the class consisting of the 1A and 2A metals of pyrosulfate, of the various phosphates, of phosphorous pentaoxide, and of dimethyl sulfoxide; $Al_2O_3$, $Mo_2O_3$, $W_2O_3$, and combinations thereof; followed by hydrogenation.

10 Claims, No Drawings

PREPARATION OF 2,3-DIHYDROFURAN

CROSS-REFERENCE

This application is a continuation-in-part of our co-pending U.S. patent application bearing Ser. No. 725,603, filed September 22, 1976 and relating to "A Process for the Preparation of Gamma-Hydroxytetrahydrofuran and Tetrahydrofuran by the Hydroformylation of Allyl Alcohol" now abandoned, which, in turn, is a division of our U.S. patent application bearing Ser. No. 629,168, filed Nov. 5, 1975, also relating to "A Process for the Preparation of Gamma-Hydroxytetrahydrofuran and Tetrahydrofuran by the Hydroformylation of Allyl Alcohol", now abandoned.

BACKGROUND OF THE INVENTION

The present invention relates to the preparation of 2-hydroxytetrahydrofuran through the utilization of a highly selective catalyst system and more specifically to the preparation of tetrahydrofuran from 2-hydroxytetrahydrofuran.

Heretofore, various catalysts have been utilized in hydroformylation reactions. Among these catalysts are various rhodium compounds or complexes such as acetyl acetonate rhodium dicarbonyl. Another specific catalyst is hydridocarbonyltris[triphenyl phosphine]rhodium which has been used in the hydroformylation of alkenes at atmospheric pressure, see *Journal of the Chemical Society* [A] 1970, Pages 2753-2764. Additionally, similar rhodium compounds or complexes have been utilized to prepare 1,4-butanediol as set forth in *U.S. Defensive Publication* No. T904,021 or to hydroformylate alpha-olefins as in U.S. Pat. No. 3,527,809 and the *Journal of Organic Chemistry*, Vol. 34, No. 2, February, 1969, pp. 327-330.

Applicant's process relates to the preparation and production of 2-hydroxytetrahydrofuran utilizing a rhodium complex which has been found to be very selective to the formation of a specific intermediate which readily yields said 2-hydroxytetrahydrofuran compound.

Additionally, tetrahydrofuran is readily prepared from 2-hydroxytetrahydrofuran by dehydration followed by hydrogenation. Although the literature reports that substituted 2hydroxytetrahydrofuran can be dehydrated by simple distillation, Botteghi et al, *Journal of Organic Chemistry*, Volume 37, No. 11, 1972, pp. 1835-1837, it has been found that non-substituted 2-hydroxytetrahydrofuran cannot be dehydrated except with the use of specific dehydration catalysts. Moreover, the prior art in dehydrating substituted 2-hydroxytetrahydrofuran often utilizes acid catalysts such as anhydrous oxalic acid, copper sulfate, ammoniun nitrate, and the like, Botteghi, *Gazzetta Chimica Italiana*, 105 (1975) pp. 233-245. However, the effect of such acid catalysts upon a non-substituted 2-hydroxytetrahydrofuran solution would result in chain opening of the furan ring to yield an aldehyde compound and, thus, prevent any possible formation of tetrahydrofuran. On the contrary, the catalysts of the present invention will readily permit dehydration of non-substituted 2-hydroxytetrahydrofuran.

SUMMARY OF THE INVENTION

It is, therefore, an object of the present invention to provide a process for the preparation of 2-hydroxytetrahydrofuran.

It is another object of the present invention to prepare 2-hydroxytetrahydrofuran, as above, through the hydroformylation of allyl alcohol.

It is a further object of the present invention to prepare 2-hydroxytetrahydrofuran, as above, utilizing a specific catalyst which is very selective in producing a desired intermediate.

It is an additional object of the present invention to produce 2-hydroxytetrahydrofuran, as above, wherein said desired intermediate readily yields said 2-hydroxytetrahydrofuran.

It is a yet further object of the present invention to prepare 2-hydroxytetrahydrofuran, as above, utilizing various pressures and temperatures which favor the preparation of said desired intermediate.

It is yet a further object of the present invention to prepare 2-hydroxytetrahydrofuran, as above, wherein organic phosphines and organic phosphites are utilized.

It is yet a further object of the present invention to produce tetrahydrofuran from 2-hydroxytetrahydrofuran.

It is yet a further object of the present invention to produce tetrahydrofuran, as above, from 2-hydroxytetrahydrofuran through dehydration followed by hydrogenation in the presence of a catalyst.

It is yet a further object of the present invention to produce tetrahydrofuran, as above, utilizing dehydration catalysts selected from the class consisting of the 1A and 2A metals of pyrolsulfate, of the various phosphates, of phosphorous pentaoxide, and dimethyl sulfoxide; of catalysts selected from the class consisting of $Al_2O_3$, $Mo_2O_3$, $W_2O_3$, and combinations thereof.

It is yet a further object of the present invention to produce 2,3-dihydrofuran, as above, wherein a cold solution containing 2-hydroxytetrahydrofuran is added to a hot catalyst, or wherein said 2-hydroxytetrahydrofuran and said catalyst are heated, or wherein said 2-hydroxytetrahydrofuran, in a liquid state, is added to a support containing thereon the above-noted dehydration catalysts.

These and other objects of the present invention, together with the advantages thereof over existing prior art processes and methods, which will become apparent from the following specification, are accomplished by the processes and methods herein described and claimed.

Generally, a process for the preparation of dihydrofuran from 2-hydroxytetrahydrofuran, comprises the steps of: heating a dehydration catalyst to a temperature of from about 130° C. to about 500° C.; contacting the 2-hydroxytetrahydrofuran with said dehydration catalyst to form said dihydrofuran, said catalyst selected from the class consisting of the 1A and 2A metals of pyrolsulfate, of the various phosphates, of phosphorous pentaoxide, and of dimethyl sulfoxide; or from the class consisting of $Al_2O_3$, $Mo_2O_3$, $W_2O_3$, and combinations thereof; and utilizing an amount of said catalyst to convert a portion of 2-hydroxytetrahydrofuran to said dihydrofuran.

DESCRIPTION OF THE PREFERRED EMBODIMENTS

According to the concept of the present invention, 2-hydroxytetrahydrofuran is prepared from allyl alcohol using a highly selective catalyst as well as various favorable reaction conditions. Additional concepts relate to the production of tetrahydrofuran from 2-hydroxytetrahydrofuran.

A preferred and specific catalyst utilized in the present invention is RhHCO[PPh$_3$]$_3$ wherein Ph stands for the phenyl radical. Utilization of the specific catalyst in accordance with various reaction conditions in the hydroformylation of allyl alcohol strongly favors the production of 4-hydroxy-n-butanal in contrast to a small amount of 2-methyl-3-hydroxypropanal. Generally, the tautomerism between 2-hydroxytetrahydrofuran and 4-hydroxy-n-butanal is highly favorable to 2-hydroxytetrahydrofuran. Amounts generally in excess of 80 percent and usually above 90 percent of a theoretical amount of 2-hydroxytetrahydrofuran can be prepared according to the present invention. The amount of catalysts utilized can vary from about 0.05 millimoles to about 50 millimoles based upon 100 grams of allyl alcohol. A preferred range extends from about 0.1 to about 5.0 millimoles with the highly preferred range generally being approximately 1.0 millimoles per 100 grams of allyl alcohol.

Generally, the catalyst is added to the solution in a suitable medium such as toluene, benzene, and other aromatic hydrocarbon solvents. Of course, any concentration may be utilized such as one millimole of catalyst per 100 milliliters of toluene. The catalyst is generally added to any conventional reaction vessel and preferably to a vessel which is equipped with a temperature-controlling device, a stirrer and exit ports which may be utilized for distillation.

The reaction vessel is also charged with a solution medium or solvent in which the hydroformylation of allyl alcohol may be carried out. Generally, a high boiling liquid is preferred which does not react with any of the various components. Specific compounds include benzene, cyclohexane, ethyl acetate, mineral oil, and generally any of the phthalates such as dioctyl phthalate.

The reactor is also charged with an organic phosphine or an organic phosphite, preferably triphenyl phosphine or triphenyl phosphite. A mole excess is utilized based upon the amount of catalyst. The excess may range from about 5 to about 150 or more, preferably from about 40 to about 110. A highly preferred excess ranges from about 55 to about 100. An excess of triphenyl phosphine and triphenyl phosphite has been found to suppress hydrogenation and to increase selectivity of the catalyst in forming 4-hydroxy-n-butanal as opposed to 2-methyl-3-hydroxypropanal. The 4-hydroxy-n-butanal is a tautomer of 2-hydroxytetrahydrofuran.

Once the reaction vessel has been charged with the catalyst and a suitable solvent such as dioctyl phthalate and triphenyl phosphine, it is then pressurized with a mixture of hydrogen and carbon monoxide. The pressure may range from about 1 atmosphere (0.10 MPa) to about 100 (10.1 MPa) atmospheres with a preferred range being from about 5 (0.51 MPa) to about 50 (5.1 MPa) atmospheres. A highly preferred range for the present invention is from about 10 (1.01 MPa) to about 12 (1.22 MPa) atmospheres. The ratio of hydrogen to carbon monoxide may vary from about 0.75 to about 5.0 and preferably from about 0.80 to about 3.0. A highly preferred range is generally from about 1 to 1 on a mole basis.

The mixture is then stirred and heated to a temperature of between about 25 and 150° C. with a preferred range being from about 50° C. to about 150° C. A highly preferred range is from about 75° C. to about 120° C. Generally, temperatures in excess of 150° C. are avoided since the catalyst loses its selectivity.

The present invention is generally carried out in a continuous operation although a batch or semi-continuous process may be utilized. In a continuous process, the allyl alcohol is added to the reaction vessel under the above-noted operating conditions. Upon reformation of 4-hydroxy-n-butanal which is in dynamic equilibrium with 2-hydroxytetrahydrofuran, the latter component is generally distilled off through a distillation port of the reaction vessel.

According to the above-noted reaction conditions, a very high amount of normal aldehyde is formed in contrast to an aldehyde containing a side chain.

The invention will be better understood by the following example which relates to the formation of 2-hydroxytetrahydrofuran.

EXAMPLE I

A 1 liter glass reactor equipped with a temperature-controlling device, a stirrer and exit ports for distillation was utilized. The reactor was charged with a solution of triphenyl phosphine (100 g) in 400 ml of dry toluene and a solution of RhHCO[PPh$_3$]$_3$, 1 m mol in 100 ml of dry toluene. The reactor was pressurized with a 1 to 1 mixture of carbon monoxide and hydrogen to 1.13 MPa (150 psig). After the mixture was stirred at 93° C. for 1.0 hour, solvent was distilled off under vacuum. One mole of allyl alcohol was then charged to the reactor. The hydroformylation was carried out at 93° C. under 1.48 MPa (200 psig) of constant 1 to 1-H$_2$/CO for 30 minutes. After the hydroformylation was completed, the product was collected by distillation at 100° C. at 2.5 mm of Hg (333 Pa). A conversion to hydroxyalkanal or 4-hydroxy-n-butanal was 82 percent. Analysis of the product in a manner as set forth in Example II shows that at least 80 percent of the product was 2-hydroxytetrahydrofuran.

The determination that the hydroformylated product of allyl alcohol was, in fact, 2-hydroxytetrahydrofuran was made as set forth in Example II.

EXAMPLE II

PREPARATION OF γ-BUTYROLACTONE FROM HYDROFORMYLATED ALLYL ALCOHOL

To a suspension of fresh silver oxide, prepared from 60 g of silver nitrate and 28 g of sodium hydroxide in 30 ml of distilled water, was added, drop-wise to a solution of hydroformylated allyl alcohol (15 g), 2 hydroxytetrahydrofuran in 15 ml of distilled water with a magnetic stirring at 0° C. for 30 minutes. After the addition was completed, the mixture was allowed to stir at room temperature for 60 minutes. The silver and excess silver oxide was filtered and washed with 50 ml of distilled water. The combined filtrate was acidified with concentrated hydrochloric acid and was evaporated at 60° C. under vacuum to remove water. The residue was extracted with methanol and then the methanol solution was removed under vacuum. A viscous liquid was collected at 100° C./5 mm of Hg (666 Pa), 12 g (82 percent). The distilled product was confirmed at γ-butyrolactone by infrared, proton magnetic resonance and mass spectra.

The following examples relate to the formation of 2-hydroxytetrahydrofuran.

EXAMPLE III

A hydroformylation reaction was carried out in a manner identical with Example I except that the 100 grams of triphenyl phosphine was added in 200 grams of toluene. The reaction was carried out for four hours, the percent conversion to 4-hydroxyalkanal was 85 percent, with approximately 84 percent of the product being 2-hydroxytetrahydrofuran.

EXAMPLE IV

The hydroformylation reaction was carried out in a manner identical to Example I except that 10 grams of triphenyl phosphine and 150 grams of dioctylphthalate was utilized. After a reaction time of 3.4 hours, a conversion to 4-hydroxyalkanal of 86 percent was obtained. Analysis showed that at least 84 percent of the product was 2-hydroxytetrahydrofuran.

EXAMPLE V

Another hydroformylation reaction was carried out identical to that in Example I except that the reaction time was 50 minutes. A conversion of 77 percent was obtained with analysis showing that the 2-hydroxytetrahydrofuran content was at least 76 percent.

EXAMPLE VI

Another hydroformylation reaction was carried out in a manner identical with Example I except that the pressure was 150 psig (1.13 MPa) at a reaction time of 36 minutes. The conversion to 4-hydroxyalkanal was 82 percent with at least 81 percent of the product being 2-hydroxytetrahydrofuran.

According to further concepts of the present invention, 2-hydroxytetrahydrofuran can be readily converted to 2-dihydrofuran by dehydration with subsequent hydrogenation to yield tetrahydrofuran.

The dehydration reaction is generally carried out at a temperature of from about 130° C. to about 500° C. and usually within a temperature range dependent upon the type of dehydration reaction utilized. Generally, any dehydration method may be utilized with the following reaction methods being desirable. One such method involves the addition of a cold or ambient temperature 2-hydroxytetrahydrofuran solution, which is in equilibrium with its tautomer of 4-hydroxy-n-butanal, to a hot catalyst at a slow rate as in a drop-wise manner. The temperature of the hot catalyst may range from about 130° C. to about 500° C. with a preferred temperature range being from about 180° C. to about 400° C. Another method simply involves adding the cold or ambient temperature 2-hydroxytetrahydrofuran solution to the catalyst which is also at ambient temperature, and then heating the entire mixture to produce the dihydrofuran. The temperature range of the heated mixture is identical to the previous method, that is from 130° C. to about 500° C. with a temperature of from about 180° C. to about 400° C. being preferred. Yet another method involves adding a cold or ambient temperature 2-hydroxytetrahydrofuran solution onto a heated or hot support bed containing a dehydration catalyst thereon. According to this method, the temperature of the support bed can range from about 150° C. to about 500° C. Regardless of the method utilized, since the boiling point of 2-hydroxytetrahydrofuran is approximately 230° C. and since the boiling point of dihydrofuran ranges from about 50° C. to about 56° C., whenever the temperature of the catalyst is generally below 230° C., only the formed product, that is dihydrofuran, will exist as a gas and hence can be collected in any conventional manner as by a condenser, a cold trap, or the like. However, if the particular method utilized is carried out at a dehydration catalyst temperature of about 230° C. or greater, of course, any non-dehydrated 2-hydroxytetrahydrofuran will also be carried over into any condensation collection device. Thus, it is necessary to separate the 2-hydroxytetrahydrofuran from the dehydrated product of dihydrofuran. This may be accomplished as through simple distillation wherein the mixture is heated at a temperature of from about 50° C. to about 225° C. and preferably at a temperature at or just above the temperature of the dihydrofuran, that is, from about 56° C. to about 60° or 65° C.

Regardless of the reaction method utilized, the various reactions are carried out in a closed vessel in the presence of an inert gas such as nitrogen, helium, and the like, to prevent oxidation of the aldehyde tautomers (that is, 4-hydroxy-n-butanal and 3-hydroxy-2-methylpropanal), to carboxylic acid and to prevent reaction of any produced olefin compound. The reaction may be carried out in a purged vessel or preferably a non-purged vessel since purging tends to blow some of the hydrofuran product out of the vessel, even if cold traps and condensers are utilized. If the reaction occurs in a purged vessel, the reaction preferably is carried out at or slightly above the atmospheric pressure, for example, from 1.01 to about 13 atmospheres, although higher pressures of up to about 5, 10, 20, etc., atmospheres may be utilized and hence, the pressure of the inert gas added is the same or slightly higher than the pressure of the vessel. Naturally, cold traps or a condenser are utilized to condense and collect the product and, hence, prevent it from being purged out of the vessel.

When the reaction is carried out in a totally enclosed vessel, that is, when a purge is not utilized, the pressure in the vessel may range from atmospheric up to about 20 atmospheres, but desirably up to 5 atmospheres, with from 1.3 atmospheres to about 2.6 atmospheres being preferred. Generally, the vessel is filled with the inert gas preferably at atmospheric pressure or at a pressure up to about 2.5 atmospheres, and totally sealed. Then, the catalysts or the entire vessel is heated to the desired temperature with the reaction pressure within the vessel, of course, being determined by the temperature. Naturally, the boiling points of the dihydrofuran and the 2-hydroxytetrahydrofuran will be elevated and the amount of elevation will correspond directly to the reaction pressure of the vessel. The increase in boiling point, of course, can be readily determined by one skilled in the art and will vary depending upon the reaction pressure. For a particular reaction method utilized, if it is desired that the 2-hydroxytetrahydrofuran not be vaporized, of course, the temperature of the catalysts and/or the 2-hydroxytetrahydrofuran should be kept below the elevated boiling point of the 2-hydroxytetrahydrofuran. On the other hand, if the reaction is carried out at a temperature which causes the 2-hydroxytetrahydrofuran to boil, even under the increased pressure, the condensed vapors can be readily separated by distillation. Generally, the distillation step can be carried out at atmospheric pressure.

It is critical to the present invention that a dehydration catalyst be utilized. Otherwise, dehydration will not occur but rather, upon heating, a polymer will be formed due to the aldo condensation reaction of the aldehyde tautomers as set forth in Example VIII. The dehydration catalysts of the present invention are solid and, hence, will form a heterogeneous solution with the 2-hydroxytetrahydrofuran with the exception of the dimethyl sulfoxide catalyst. Thus, agitation or mixing is commonly utilized. The catalysts of the present invention include the 1A and 2A metals of pyrosulfate, of the various phosphates, of phosphorous pentaoxide, and of dimethyl sulfoxide. Additionally, the dehydration catalysts also include $Al_2O_3$, $Mo_2O_3$, $W_2O_3$, and combinations thereof. Generally, the amount of any particular metal oxide catalyst in a blend of a metal oxide catalyst may, of course, range from a trace (i.e., from about 0.1 percent), up to 99.9 percent plus, by weight. A highly preferred catalyst is potassium pyrosulfate ($K_2S_2O_7$). In order to produce high yields of dihydrofuran, it is highly desirable to use the various catalysts in a completely dry state, that is, free from any water. Generally, the range of the above catalysts is from about 0.05 moles to about 1.0 mole per mole of 2-hydroxytetrahydrofuran with a preferred range being from about 0.1 to about 0.6 moles, with the exception of dimethyl sulfoxide wherein a suitable range is from about 2.0 to about 15 moles and, preferably, from about 5 to about 8 moles per mole of 2-hydroxytetrahydrofuran.

Generally, the catalysts of $Al_2O_3$, $Mo_2O_3$, or $W_2O_3$, or combinations thereof, are used as a support catalyst. That is, these catalysts, since they are very difficult to make in powdered form, are generally bound or held together with a suitable binder such as a silica gel, and placed upon a porous support such as clay, fire brick, a metal lattice, or any conventional support bed. Of course, the various other catalysts set forth above can also be utilized and coated on a support. The amount of the metal oxide support catalysts, as well as the other catalysts in comparison with the binder, for example, silica gel, will generally range from about 0.1 percent to about 20 percent by weight.

The invention will be better understood by the following examples.

EXAMPLE VII

To a 100 ml three neck flask equipped with a nitrogen bubbler, addition funnel, thermometer and magnetic stirrer in a vigeraux column was added 2.5 g of potassium pyrosulfate. The catalyst was then heated to a temperature of 225° C. A solution of 2-hydroxytetrahydrofuran (22.0 g, 0.25 moles) at 25° C. was added at about 15 to about 20 drops per minute and gave a distillate of from about 35° C. to about 58° C. The receiver contained 5.5 g of a mixture of water and 2,3-dihydrofuran. Two −78° C. cold traps were utilized which contained a total weight, respectively, of 5.7 and 3.0 g of the $H_2O$ olefin mixture. This product, collected at −78° C., consisted of 5.1 and 2.5 g of 2,3-dihydrofuran (identified by I.R. and gas chromatography) and 0.6 and 0.5 g of ice. No 2,3-dihydrofuran was isolated by freezing the distillate in the receiver, but from the theoretical yield of water expected, this must contain an additional 2.0 g of product.

The residue in the flask was a red-brown solid which, upon cooling, adhered so well to the flask that sections of glass were pulled from the wall. The residue was separated from the glass by powdering and floating it on chloroform followed by decanting the mixture from the precipitated powdered glass. The chloroform extracted 0.9 g (4.1 percent) of what appeared to be the isomeric 2-methyl-3-hydroxypropanal and left a residue of 8.8 g of insoluble resin and potassium pyrosulfate. This solid resin was then extracted with hot water to give 5.3 g (30 percent) of what appeared to be polymerized 2,3-dihydrofuran. Thus, from this reaction, 4 percent of the hydroformylation mixture did not dehydrate to 2,3-dihydrofuran. The products obtained were 30 percent of 2,3-dihydrofuran that was polymerized by the acidic catalyst, 49 percent of 2,3-dihydrofuran was isolated, 6 percent was lost by partial solubility in the water generated during the reaction, and 11 percent was swept past the two −78° C. cold traps by the nitrogen purge.

In a similar example wherein the catalyst, potassium pyrosulfate, was wet, a smaller amount of 2,3-dihydrofuran was isolated (17 percent) with 43 percent polymer and 40 percent volitalization loss. Of course, as noted, it is highly desirable to utilize a dry catalyst.

EXAMPLE VIII

Fifty grams of a feed stock at an ambient temperature containing 87.27 percent of 2-hydroxytetrahydrofuran in equilibrium with its tautomer of 4-hydroxy-n-butanal and approximately 11.94 percent by weight of 3-hydroxy-2-methylpropanal was added to a 100 milliliter volume distillation flask equipped with a magnetic stirrer and thermometer. The flask was placed in an oil bath and heated slowly up to 230° C. over a period of time of 3 hrs. At temperatures of approximately 56° C. and slightly above, which is the boiling point of 2,3-dihydrofuran, no distillate, whatsoever, was obtained. Upon heating at temperatures above 56° C., a polymer was formed in the flask. During the entire distillation period, only a trace of distillate (water), less than 1 g, was obtained. The amount of distillate was dried over potassium carbonate and was then extracted with ether. The ether solution was then fractionally distilled wih only ether being obtained. No 2,3-dihydrofuran and no 2-hydroxytetrahydrofuran was obtained. The polymer formed was the aldo condensation of the aldehyde tautomer of 2-hydroxytetrahydrofuran (4-hydroxy-n-butanal) with itself and with 3-hydroxy-2-methylpropanal.

Thus, Example VIII clearly shows that the lack of any dehydration catalysts of the present invention does not result in the production of any 2,3-dihydrofuran, but rather results in a polymer.

The produced 2,3-dihydrofuran may be hydrogenated in any conventional or known manner or method well known to those skilled in the art. Generally, the hydrogenation reaction can be carried out at temperatures ranging from −20° C. to about 500° C. However, a preferred range is from about 0° C. to about 150° C. The pressure may range from about 1 (0.10 MPa) atmosphere to about 15,000 psig (103 MPa) with a more desirable range being from 1 (0.10 MPa) atmosphere to about 3,000 psig (20.7 MPa). A preferred range is from about 25 psig (0.273 MPa) to about 2,000 psig (13.9 MPa).

With respect to the catalyst system employed, generally, any conventional or well known catalyst may be utilized. That is, various known cobalt, nickel and iron catalyst complexes may be employed. Specific examples of desirable catalysts include Raney nickel, Raney cobalt, and the like. Additionally, examples of hydrogenated catalysts include those specifically set forth in U.S. Pat. Nos. 3,625,927; 3,868,354; 3,872,072; and 3,882,094, which are specifically incorporated by reference, particularly with respect to the preparation and the catalyst produced.

The hydrogenation process can be carried out in any conventional manner well known to those skilled in the art and readily yields tetrahydrofuran.

Of course, the tetrahydrofuran produced may be utilized as a solvent as well as a starting material for the preparation of various polymers such as polyurethanes.

While in accordance with the patent statutes, preferred embodiments have been illustrated and described in detail, it is to be understood that the invention is not limited thereto, the invention being measured solely by the scope of the attached claims.

What is claimed is:

1. A process for the preparation of 2,3-dihydrofuran from 2-hydroxytetrahydrofuran, comprising the steps of:
    heating a dehydration catalyst to a temperature of from about 130° C. to about 500° C.;
    contacting the 2-hydroxytetrahydrofuran with said dehydration catalyst to form the 2,3-dihydrofuran, said catalyst selected from the class consisting of the 1A and 2A metals of pyrosulfate, phosphorous pentaoxide, and dimethyl sulfoxide; or from the class consisting of $Al_2O_3$, $Mo_2O_3$, $W_2O_3$, and combinations thereof; and
    utilizing a sufficient amount of said catalyst to convert a portion of 2-hydroxytetrahydrofuran to said 2,3-dihydrofuran.

2. A process according to claim 1, wherein said catalyst is located on a support, and said support having said catalyst thereon is heated to a temperature ranging from about 150° C. to about 500° C.

3. A process according to claim 2, wherein said support catalysts are selected from the class consisting of $Al_2O_3$, $Mo_2O_3$, $W_2O_3$, and combinations thereof.

4. A process according to claim 2, wherein said catalyst on said support is potassium pyrosulfate.

5. A process according to claim 1, wherein said 2-hydroxytetrahydrofuran is contacted with said catalyst by adding it to said heated dehydration catalyst, the amount of said catalyst ranging from about 0.05 to about 1.0 mole per mole of said 2-hydroxytetrahydrofuran with the exception of said dimethyl sulfoxide catalyst which has a range of from about 2.0 to about 15 moles per mole of 2-hydroxytetrahydrofuran.

6. A process according to claim 5, wherein said catalyst is selected from said class consisting of said 1A and 2A metals of said pyrosulfate, said phosphorous pentaoxide, and said dimethyl sulfoxide, and
    adding an amount of said catalyst ranging from about 0.1 to about 0.6 moles per mole of 2-hydroxytetrahydrofuran and from about 5 moles of about 8 moles when said catalyst is said dimethyl sulfoxide.

7. A process according to claim 6, wherein said catalyst is potassium pyrosulfate, and wherein said catalyst is heated to a temperature of from about 180° C. to about 400° C.

8. A process according to claim 1, including contacting said 2-hydroxytetrahydrofuran with said dehydration catalyst by adding said 2-hydroxytetrahydrofuran and said dehydration catalyst to a vessel, the amount of said catalyst ranging from about 0.05 to about 1.0 mole per mole of said 2-hydroxytetrahydrofuran with the exception of said dimethyl sulfoxide catalyst which has a range of from about 2.0 to about 15 moles per mole of 2-hydroxytetrahydrofuran, and
    subsequently carrying out said heating step of said dehydration catalyst as well as heating said 2-hydroxytetrahydrofuran.

9. A process according to claim 8, wherein said catalyst is selected from said class consisting of said 1A and 2A metals of said pyrosulfate, said phosphorous pentaoxide, and said dimethyl sulfoxide, and
    adding an amount of said catalyst ranging from about 0.1 to about 0.6 moles per mole of 2-hydroxytetrahydrofuran and from about 5 moles to about 8 moles when said catalyst is said dimethyl sulfoxide.

10. A process according to claim 9, wherein said catalyst is potassium pyrosulfate, and said catalyst is heated to a temperature of from about 180° C. to about 400° C.

* * * * *